United States Patent [19]

Love et al.

[11] Patent Number: 5,414,090
[45] Date of Patent: May 9, 1995

[54] LUBRICANT ASHLESS ANTIWEAR-ANTIOXIDANT ADDITIVE

[75] Inventors: Doris Love, Fishkill; Julian H. Dancy, Poughkeepsie; Jayne M. Lucas, Campbell Hall, all of N.Y.

[73] Assignee: Texaco Inc., White Plains, N.Y.

[21] Appl. No.: 144,376

[22] Filed: Nov. 2, 1993

[51] Int. Cl.$^6$ ................ C07D 285/12; C10M 135/36
[52] U.S. Cl. ..................................... 548/142; 252/47.5
[58] Field of Search ........................ 548/142; 252/47.5

[56] References Cited

U.S. PATENT DOCUMENTS 5,026,805 6/1991 Karol ................................. 548/142
5,172,212 1/1993 Karol ................................. 548/142

*Primary Examiner*—Robert Gerstl
*Attorney, Agent, or Firm*—George J. Darsa

[57] ABSTRACT

An adduct of 2,5-dimercapto-1,2,4-thiadiazole, an epoxide, a formaldehyde and 4,4'-isopropylidenediphenol represented by the formula

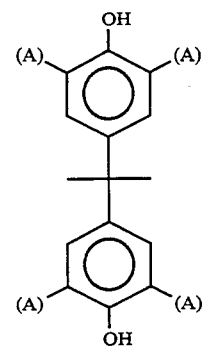

where A is H or

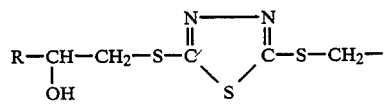

where R is H or a ($C_1$-$C_{30}$) alkyl group and n=1-4.

19 Claims, No Drawings

LUBRICANT ASHLESS ANTIWEAR-ANTIOXIDANT ADDITIVE

BACKGROUND OF THE INVENTION

This invention relates to lubricant additives, and more particularly to a novel lubricant ashless antiwear-antioxidant additive.

Generally, ashless additives have been developed because of the properties which they are intended to impart to lubricants. However, the various attempts have been expensive and not effective in imparting the desired properties in lubricants.

Thus, an object of the present invention is to provide an inexpensive, effective ashless antiwear-antioxidant lubricant additive.

DISCLOSURE STATEMENT

U.S. Pat. No. 4,906,393 discloses a mixed phenol/-dimercapto-thiadiazole-derived hydroxy - thioester borates effective as a antiwear/antioxidant multifunctional additives for lubricants.

U.S. Pat. No. 4,935,157 discloses a novel 2-hydroxy-5-alkylthio-1,3,4-thiadiazoles wherein the alkyl group may be substituted by hydroxy and phenoxy groups. The compounds are effective antiwear agents and antioxidants when incorporated into lubricating compositions.

U.S. Pat. No. 5,026,865 discloses a novel derivatives of thiadiazole compounds and their use as functional additives for oil-based and water-based lubricating compositions. More particularly the new thiadiazoles are derived from 2,5-dimercapto-1,3,4-thiadiazole and epoxy compound.

U.S. Pat. No. 5,177,212 discloses a process for making a lubricant additive where the starting material is a simple phenol and the products formed are either mono- or di-substituted on the single ring. The starting phenol also contains an alkyl substituent.

SUMMARY OF THE INVENTION

The present invention provides an adduct of 2,5-dimercapto-1,2,4-thiadiazole, an epoxide, formaldehyde and 4,4'-isopropylidene diphenol (Bisphenol A) prepared by the method represented below by Equations (1) and (2) as follows:

EQUATION (1)

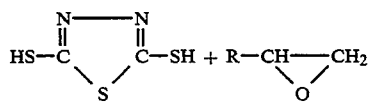

EQUATION (2)

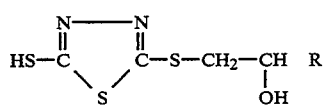

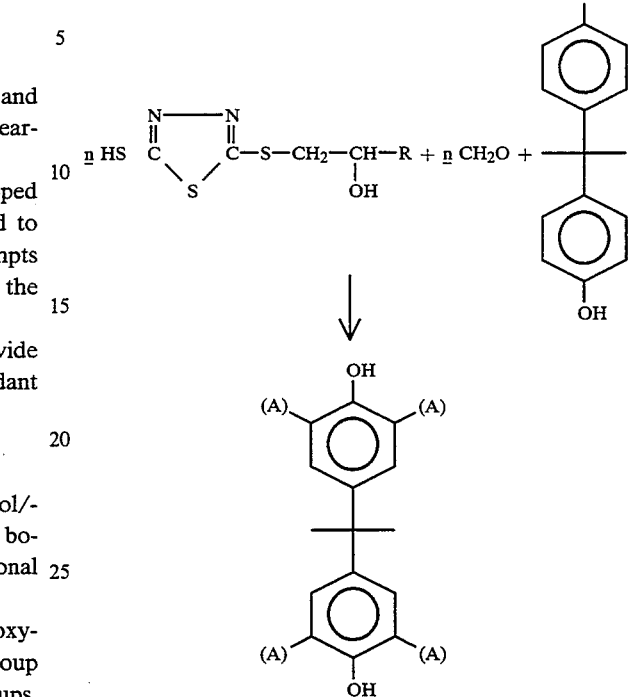

wherein R is H or a ($C_1$-$C_{30}$) alkyl group; n is an integer of 1–4; and A is H or $$R-CH-CH_2-S-C\underset{S}{\overset{N-N}{\underset{\|}{\|}}}C-S-CH_2-$$
$$\phantom{R-CH-CH_2-S-C}|\phantom{-S-C-----C-S-CH_2-}$$
$$\phantom{R-CH-CH_2-S-C}OH$$

DETAILED DESCRIPTION OF THE INVENTION

The lubricants of automobile combustion and diesel, engines are generally developed to ensure the long-lasting parts moveable and non-moving, of such engines.

The present invention is specifically designed to provide an ashless antiwear-antioxidant additive.

According to the present invention there is provided a disubstituted 2,5-dimercapto-1,3,4-thiadiazole (DMTD) ashless, antiwear-antioxidant.

In the method to produce the present antiwear-antioxidant, the starting material is Bisphenol A (i.e., 4,4'-isopropylidenediphenol). It contains two phenolic rings attached through an isopropyl linkage. There are no alkyl substituents on the individual phenolic rings and substitution may occur in four places as indicated by the arrows in the formula below:

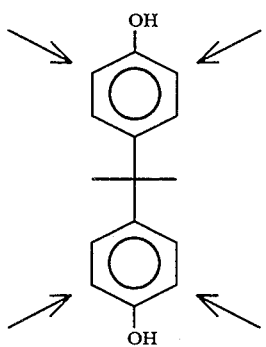

This would produce a molecule that is considerably different from those of the prior art, such as those cited in U.S. Pat. No. 5,177,212, because tetra substituted products could be prepared and there would be substitution in both rings of the molecule.

In the present invention, DMTD is reacted with an epoxide to form an intermediate (I) according to the following equation:

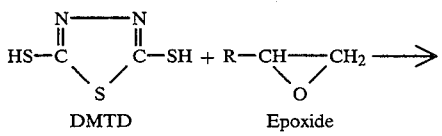

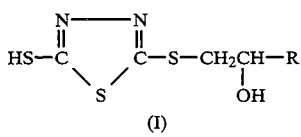

where R is H or a ($C_1$-$C_{30}$) alkyl group.

In the second step of the reaction, the intermediate is reacted with formaldehyde and Bisphenol A according to the following equation:

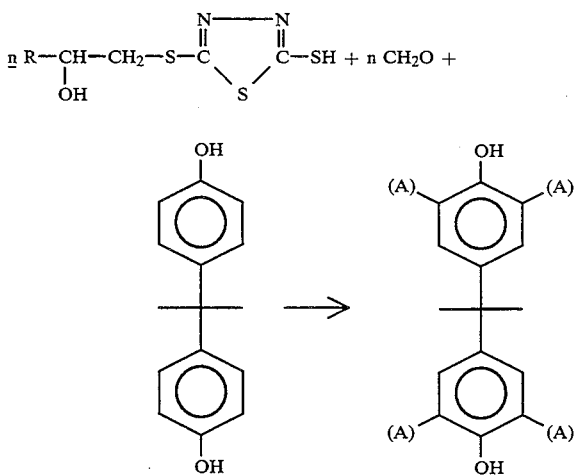

wherein R is H or a ($C_1$-$C_{30}$) alkyl group and n=1–4; and where A is H or

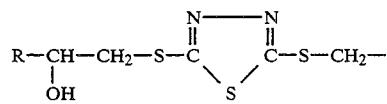

The ratio of intermediate and formaldehyde to Bisphenol A may vary from 1:1:1 to 4:4:1. Substitution may occur at as many as four separate places when the ratio is 4:4:1 or as few as one place when the ratio is 1:1:1.

In order to show the advantages of the present invention, the following Examples are provided.

EXAMPLE I

Synthesis of DMTD, Epoxide, Bisphenol A Derivative (2:2:1)

225 Grams (1.50 m) DMTD was added to stirring 519 gms. (1.50 m) of a ($C_{20}$-$C_{24}$) epoxide at ambient temperature. Mixture stirred at 150° C. for 3 hours. Cooled to ambient. 171 Gms. (0.75 m) Bisphenol A added. 135 Gms. (1.65 m) 37% aqueous formaldehyde added over ½ hour to stirring mixture at ambient. Stirred at 80° C. for 3 hours. Solvent stripped to 177° C. and stirred at 177° C. for 3 hours and filtered and providing a yield of:

| Yield | Found 836 gms. | Theory 936 gms. |
|---|---|---|
| % N | 4.33 | 4.3 |
| % S | 12.8 | 14.9 |

EXAMPLE II

Synthesis of DMTD, Epoxide, Bisphenol A Derivative (3:3:1)

150 Grams (1.0 m) DMTD was added to stirring 348 gms. (1.0) of a ($C_{20}$-$C_{24}$) epoxide at ambient temperature. Mixture stirred at 150° C. for 3 hours. Cooled to ambient. 76 Grams (0.33 m) Bisphenol A added. 90 Grams (1.10 m) 37% aqueous formaldehyde added over ½ hour to stirring mixture at ambient. Stirred at 80° C. for 3 hours. Solvent stripped to 177° C. and stirred at 177° C. for 3 hours and then filtered and providing a yield of:

| Yield | Found 497 gms. | Theory 588 gms. |
|---|---|---|
| % N | 4.74 | 4.8 |
| % S | 14.0 | 16.3 |

TEST DATA SHOWING THAT DMTD, EPOXIDE, BISPHENOL A CONDENSATION PRODUCTS ARE ANTIWEAR AGENTS

The wear performance of the antiwear additives was evaluated in a Roxana Four-Ball Wear Tester, using 12.7 mm chrome alloy steel balls. Tests were run at 600 rpm, 40 kg. load and 200° F. for 30 minutes. Test results are reported in terms of mm. average wear scar diameter. The test samples were prepared using an SAE 30 Base Blend containing dispersant, detergent and antioxidant, and adding a pro-wear contaminant and an antiwear agent. The pro-wear contaminant added represents one found in engine service and is used at a dosage which enables good discrimination between antiwear additives in a short test.

To demonstrate its effectiveness, Table I is provided wherein the performance of the new additive in the wear test was compared to that of a known, effective ZDTP antiwear additive. The concentration of ZDTP antiwear additive in the test oil is identified by percent phosphorus, and the concentration of the new additive by percent sulfur.

TABLE I (SAE 30 OIL)

| Run No. | Additive | % S | % P | Four Ball Wear Test (Wear Scar Diameter mm) |
|---|---|---|---|---|
| 1. | Typical ZDTP | — | 0.14 | 0.42 |
| 2. | Typical ZDTP | — | 0.05 | 0.61 |
| 3. | Example I | 0.14 | — | 0.34 |
| 4. | Example I | 0.05 | — | 0.48 |
| 5. | Example II | 0.14 | — | 0.38 |
| 6. | Example II | 0.05 | — | 0.42 |

TEST DATA SHOWING THAT DMTD-EPOXIDE-BISPHENOL A CONDENSATION PRODUCTS ARE ANTIOXIDANTS

All additives were evaluated in a Bench Oxidation Test(BOT). The evaluations are set forth below in Table II. In the BOT, the additive (1.0 or 0.5wt. %), overbased (ob) sulfonate (0.18% Ca) and SNO-150 were heated to 175° C. under $N_2$ and a sample taken (base line). The mixture was then stirred at 175° C. under a stream of air at 500 ml/min. for six hours. Samples were taken every hour and the DIR of each sample was determined against the baseline at 1712 cm-1. The six hour DIR was used as a measure of oxidation; the smaller the value, the better the antioxidant properties.

TABLE II

BOT RESULTS

| Sample | No Additive | 1 W % Additive | 0.5 W % Additive |
|---|---|---|---|
| SNO-150 + ob sulfonate + No Additive | 17.0–20.0 | — | — |
| SNO-150 + ob sulfonate + ZDTP | — | 6.1 | — |
| SNO-150 + ob sulfonate + commercial antioxidant | — | 9.8 | 11.5 |
| SNO-150 ob sulfonate Example I | — | — | 2.32 |
| SNO-150 + ob sulfonate Example II | — | 2.57 | 2.64 |

We claim:

1. An adduct of 2,5-dimercapto-1,2,4-thiadiazole represented by the formula:

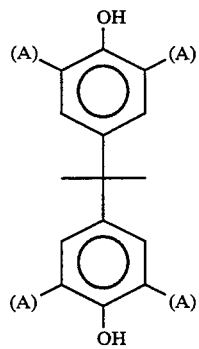

wherein A is H or

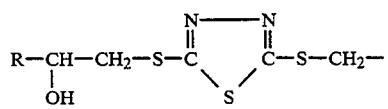

and at least one A is

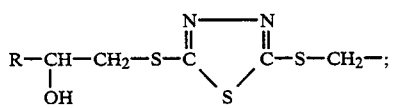

and R is H or a $(C_1-C_{30})$ alkyl group.

2. An adduct according to claim 1, wherein R is a $C_{20}-C_{24}$-alkyl.

3. An adduct according to claim 1, wherein one A is

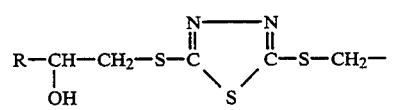

and the remaining A's are H.

4. An adduct according to claim 1, wherein two A's are H and the remaining A's are

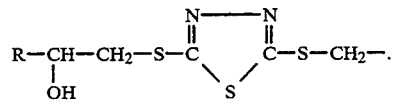

5. An adduct according to claim 1, wherein one A is H and the remaining A's are

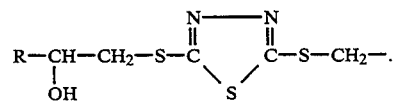

6. An adduct according to claim 1, wherein all of the A's are

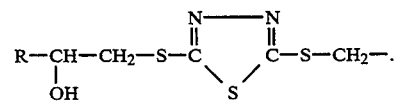

7. An ashless antiwear-antioxidant additive product obtained by:

(a) reacting 2,5-dimercapto-1,3,4-thiadiazole with an epoxide to provide an intermediate product represented by the reaction equation:

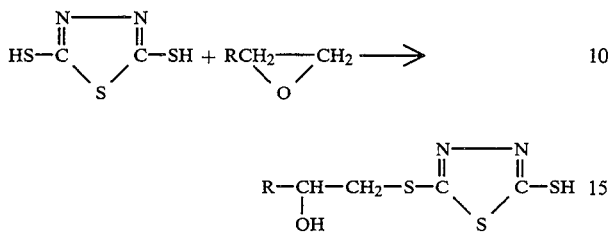

(b) forming an adduct by reacting said intermediate product with formaldehyde and a phenol represented by the reaction equation

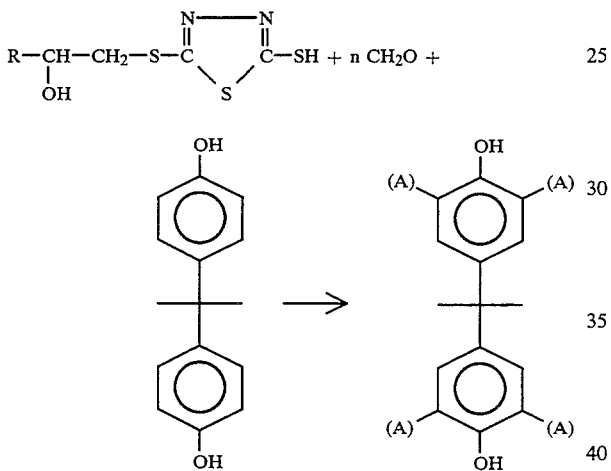

wherein A is H or

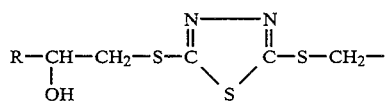

and at least one A is

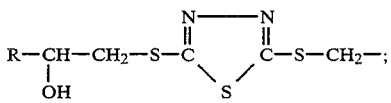

R is H or a ($C_1$-$C_{30}$) alkyl group; and n is 1–4.

8. The product of claim 7, wherein a ratio of the thiadiazole to said epoxide to said 4,4' isopropylidenediphenol ranges from about 1:1:1 to about 4:4:1.

9. The product of claim 8, wherein the ratio is 1:1:1.

10. The product of claim 8, wherein the ratio is 2:2:1.

11. The product of claim 8, wherein the ratio is 3:3:1.

12. The product of claim 8, wherein the ratio is 4:4:1.

13. The product of claim 7, wherein R is $C_{20}$-$C_{24}$-alkyl.

14. A lubricating oil composition comprising a lubricating oil and effective amount of an adduct according to claim 1.

15. A lubricating oil composition comprising a lubricating oil and effective amount of an adduct according to claim 2.

16. A lubricating oil composition comprising a lubricating oil and effective amount of an adduct according to claim 3.

17. A lubricating oil composition comprising a lubricating oil and effective amount of an adduct according to claim 4.

18. A lubricating oil composition comprising a lubricating oil and effective amount of an adduct according to claim 5.

19. A lubricating oil composition comprising a lubricating oil and effective amount of an adduct according to claim 6.

* * * * *